(12) United States Patent
Sakaguchi

(10) Patent No.: US 10,278,874 B2
(45) Date of Patent: May 7, 2019

(54) DISPOSABLE DIAPER

(71) Applicant: UNICHARM CORPORATION, Shikokuchuo-shi, Ehime (JP)

(72) Inventor: Satoru Sakaguchi, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 244 days.

(21) Appl. No.: 14/359,902

(22) PCT Filed: Nov. 21, 2012

(86) PCT No.: PCT/JP2012/080182
§ 371 (c)(1),
(2) Date: May 21, 2014

(87) PCT Pub. No.: WO2013/077360
PCT Pub. Date: May 30, 2013

(65) Prior Publication Data
US 2014/0364827 A1    Dec. 11, 2014

(30) Foreign Application Priority Data

Nov. 22, 2011 (JP) ................................. 2011-255249

(51) Int. Cl.
*A61F 13/49*    (2006.01)
*A61F 13/536*    (2006.01)

(52) U.S. Cl.
CPC .. *A61F 13/49017* (2013.01); *A61F 13/49001* (2013.01); *A61F 13/536* (2013.01); *A61F 2013/49039* (2013.01)

(58) Field of Classification Search
CPC ...... A61F 13/49017; A61F 2013/49039; A61F 13/49001; A61F 13/49453; A61F 13/536; A61F 2013/49022

(Continued)

(56) References Cited

U.S. PATENT DOCUMENTS 4,425,129 A * 1/1984 Karami ............. A61F 13/49019
604/385.26
4,515,595 A * 5/1985 Kievit ............... A61F 13/49011
604/385.3

(Continued)

FOREIGN PATENT DOCUMENTS

CN    1705465 A    12/2005
CN   101674791 A    3/2010

(Continued)

OTHER PUBLICATIONS

Japanese Office Action for Japanese dated Feb. 5, 2013 w/ English language translation.

(Continued)

*Primary Examiner* — Catharine L Anderson
(74) *Attorney, Agent, or Firm* — Hauptman Ham, LLP

(57) ABSTRACT

A disposable diaper includes a front waistline region, a rear waistline region and a fastening tape, as the waistline retaining unit extending along the product widthwise direction and holding the disposable diaper onto a body of a wearer. Furthermore, the disposable diaper includes a crotch stretch unit that is formed in the crotch region and can expand and contract in the product longitudinal direction, and leg gathers. The leg gathers are longer than the crotch stretch unit in the product longitudinal direction L, and are provided at an outer side from the crotch stretch unit in the product widthwise direction. A low stretch region having a lower ratio of expansion and contraction than the crotch stretch unit is formed between the leg gathers and the crotch stretch unit.

24 Claims, 5 Drawing Sheets

(58) Field of Classification Search
USPC .................................... 604/385.25–385.28
See application file for complete search history.

(56) References Cited

U.S. PATENT DOCUMENTS

| | | | | |
|---|---|---|---|---|
| 4,704,116 A * | 11/1987 | Enloe | ............... | A61F 13/49009 604/358 |
| 4,756,942 A * | 7/1988 | Aichele | ............... | A61F 13/0273 428/102 |
| 4,775,375 A * | 10/1988 | Aledo | ............... | A61F 13/49007 604/378 |
| 4,892,536 A * | 1/1990 | DesMarais | ........ | A61F 13/49019 604/385.19 |
| 4,895,568 A * | 1/1990 | Enloe | ............... | A61F 13/4758 604/385.27 |
| 4,935,021 A * | 6/1990 | Huffman | ............. | A61F 13/5323 604/385.26 |
| 5,366,453 A * | 11/1994 | Zehner | ............. | A61F 13/49009 604/358 |
| 5,370,634 A | 12/1994 | Ando et al. | | |
| 5,634,917 A * | 6/1997 | Fujioka | ............. | A61F 13/49019 604/373 |
| H1687 H * | 10/1997 | Roe | ................... | A61F 13/47227 604/378 |
| 5,683,531 A * | 11/1997 | Roessler | .......... | A61F 13/15593 156/163 |
| 5,855,573 A * | 1/1999 | Johansson | ............. | A61F 13/496 2/401 |
| 6,482,195 B1 * | 11/2002 | Kumasaka | ........ | A61F 13/49017 604/385.21 |
| 6,500,161 B1 * | 12/2002 | Freiburger | ........ | A61F 13/15203 604/385.01 |
| 6,648,869 B1 * | 11/2003 | Gillies | ............... | A61F 13/51104 604/385.101 |
| 7,344,524 B2 * | 3/2008 | Cazzato | ............ | A61F 13/49011 604/385.25 |
| 9,333,121 B2 * | 5/2016 | Sakaguchi | ............. | A61F 13/494 |
| 9,517,167 B2 * | 12/2016 | Sakaguchi | ........ | A61F 13/49413 |
| 9,592,164 B2 * | 3/2017 | Sakaguchi | ........ | A61F 13/49001 |
| 2002/0072728 A1 * | 6/2002 | Shinohara | ......... | A61F 13/49017 604/385.29 |
| 2003/0040732 A1 * | 2/2003 | Ishikawa | .......... | A61F 13/49017 604/385.29 |
| 2003/0088226 A1 * | 5/2003 | Takagi | ............... | A61F 13/15593 604/385.16 |
| 2003/0120246 A1 * | 6/2003 | Franklin | ........... | A61F 13/15593 604/385.27 |
| 2004/0133181 A1 * | 7/2004 | Ishiguro | ............ | A61F 13/49001 604/385.28 |
| 2005/0055001 A1 * | 3/2005 | Cazzato | ............ | A61F 13/49011 604/385.01 |
| 2005/0096624 A1 * | 5/2005 | Hoshino | ........... | A61F 13/49019 604/385.27 |
| 2006/0089614 A1 | 4/2006 | Bonnin | | |
| 2008/0071241 A1 * | 3/2008 | Bittner | ............... | A61F 13/49014 604/385.27 |
| 2008/0300568 A1 * | 12/2008 | Fujioka | ............. | A61F 13/15593 604/385.27 |
| 2009/0312739 A1 * | 12/2009 | Umebayahi | ............ | A41B 9/001 604/385.29 |
| 2010/0094239 A1 * | 4/2010 | Nakaoka et al. | ........ | 604/385.25 |
| 2011/0098666 A1 | 4/2011 | Nakajima et al. | | |
| 2011/0184371 A1 | 7/2011 | Sakaguchi | | |
| 2012/0143162 A1 * | 6/2012 | Mukai | ............... | A61F 13/15804 604/385.3 |
| 2013/0030402 A1 * | 1/2013 | Arayama | .......... | A61F 13/49019 604/385.3 |
| 2013/0041336 A1 * | 2/2013 | Mukai | ................... | A61F 13/535 604/378 |
| 2013/0102982 A1 * | 4/2013 | Nakano | ............. | A61F 13/49019 604/365 |
| 2014/0330239 A1 * | 11/2014 | Sakaguchi | ........ | A61F 13/49001 604/385.31 |
| 2014/0358109 A1 * | 12/2014 | Sakaguchi | ........ | A61F 13/49413 604/385.26 |

FOREIGN PATENT DOCUMENTS

| | | |
|---|---|---|
| EP | 2111832 A1 | 10/2009 |
| JP | 2004-141270 A | 5/2004 |
| JP | 2010-279612 A | 12/2010 |
| WO | 2006/007226 A1 | 1/2006 |
| WO | 2009/145287 A1 | 12/2009 |
| WO | 2010/038708 A1 | 4/2010 |
| WO | 2010/140678 A1 | 12/2010 |
| WO | 2011/105108 A1 | 9/2011 |

OTHER PUBLICATIONS

International Search Report dated Feb. 26, 2013 in International Application No. PCT/JP2012/080182, filed Nov. 21, 2012.
Office Action in EG Patent Application No. 2014050815, dated Feb. 18, 2016.
Office Action in TW Patent Application No. 101142024, dated Jun. 7, 2016.
Extended European Search Report dated Jun. 9, 2015, corresponding to European patent application No. 12851187.0.
Office Action in AU Patent Application No. 2012341537, dated May 31, 2016.
Office Action dated Jan. 14, 2016, in GCC Patent Application No. 2012-22860.
Office Action dated May 6, 2015, corresponding to Chinese patent application No. 201280057547.4.
Office Action in AU Patent Application No. 2012341537 dated Sep. 20, 2016.
Office Action in AU Application No. 2012341537, dated Mar. 14, 2017.
Office Action in EP Application No. 12851187.0, dated Jun. 30, 2017.
Office Action in CN Application No. 201510708160.6, dated Mar. 26, 2018, 13pp.
Office Action in CN Application No. 201510708160.6, dated Dec. 27, 2018, 12pp.

* cited by examiner

CONVENTIONAL EXAMPLE

EXAMPLE

DISPOSABLE DIAPER

RELATED APPLICATIONS

The present application is a National Phase of International Application Number PCT/JP2012/080182, filed Nov. 21, 2012, and claims priority from Japanese Application Number 2011-255249, filed Nov. 22, 2011.

FIELD OF INVENTION

The present invention relates to a disposable diaper in which a pair of leg hole opening units are formed, and which includes an absorber running across a crotch region and extending in the front waistline region and the rear waistline region.

BACKGROUND ART

Conventionally, in order to achieve a wearing comfort while preventing the leakage of bodily waste, various methods have been devised in a disposable diaper. For example, a structure is known according to which in a disposable diaper including an absorber running across the crotch region and extending in the front waistline region and the rear waistline region, the absorber is divided into three in the product longitudinal direction, and extended elastic members are arranged along the absorber in the outer side of the product widthwise direction of the absorber (for example, Patent Literature 1).

As for the absorber that has been divided into three, at the time of wearing, the space between the adjoining absorbers is reduced and the absorbers come in contact with each other due to which the disposable diaper fits well on the wearer, and the crowding of the disposable diaper at the time of wearing is prevented.

CITATION LIST

Patent Literature

Patent Literature 1: Japanese Unexamined Patent Application Publication No. 2004-141270 (FIG. 1 and FIG. 2)

SUMMARY OF INVENTION

Technical Problem

In the aforementioned conventional disposable diaper, as a result of the contractile force of the elastic members arranged in an extended state along the absorber, there operates a force that keeps the absorber in close contact with the body of the wearer at all times.

Therefore, the contractile force of the elastic members continues to work as a force for pulling down the front waistline region and the rear waistline region of the disposable diaper in the crotch direction. Particularly, after the disposable diaper has absorbed the bodily waste, the front waistline region and the rear waistline region of the disposable diaper shift in the crotch direction, and an unnecessary space can be formed easily between the area around the legs of the wearer and the disposable diaper.

Thus, the present invention has been achieved in view of such a condition, and an object thereof is to provide a disposable diaper that runs along the body of the wearer without the crotch region coming too close to the body, and which can more surely prevent the occurrence of a space with respect to the area around the legs.

Solution to Problem

A aspect of the present invention according to the present invention is summarized as a disposable diaper (disposable diaper 10) comprising: a front waistline region (front waistline region 20); a rear waistline region (rear waistline region 30); a crotch region (crotch region 25) positioned between the front waistline region and the rear waistline region; a pair of leg hole opening units (leg hole opening units 35); an absorber (absorber 40) running across the crotch region and extending in the front waistline region and rear waistline region; a product longitudinal direction (product longitudinal direction L) from the front waistline region towards the rear waistline region; a product widthwise direction (product widthwise direction W) that is perpendicular to the product longitudinal direction; a waistline retaining unit (the front waistline region 20, the rear waistline region 30, and a fastening tape 90) extending along the product widthwise direction in the front waistline region and the rear waistline region, and holding the disposable diaper onto a body of a wearer; a crotch unit (crotch stretch unit 200a) that is formed in the crotch region and can expand and contract in at least the product longitudinal direction; and a pair of leg elastic units (leg gathers 75) that are formed along the leg hole opening units and can expand and contract in at least the product longitudinal direction; wherein the leg elastic units are longer than the crotch unit in the product longitudinal direction and are provided at an outer side from the crotch unit in the product widthwise direction; and a low stretch region (low stretch region 300) having a lower ratio of expansion and contraction than the crotch unit is formed between the leg elastic unit and the crotch unit.

Advantageous Effects of Invention

According to the aspect of the present invention, it is possible to provide a disposable diaper that runs along the body of the wearer without the crotch region coming too close to the body, and which can more surely prevent the occurrence of a space with respect to the area around the legs.

DESCRIPTION OF EMBODIMENTS

Figure 1:
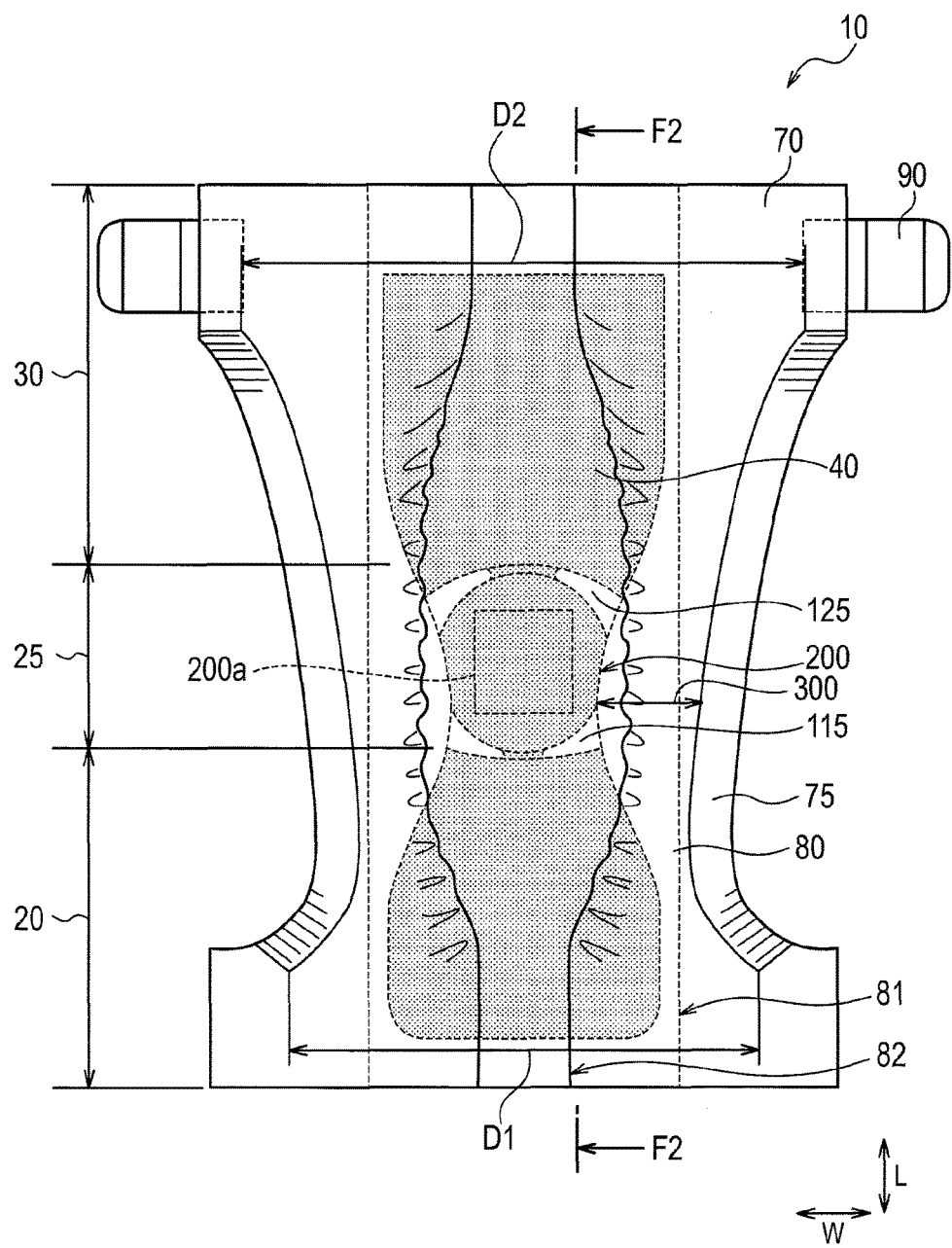
FIG. 1 is an exploded plan view of a disposable diaper 10 according to an embodiment of the present invention.

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Therefore, a specific dimension should be determined in view of the following description. Moreover, among the drawings, the respective dimensional relations or ratios may differ.

(1) Entire Schematic Configuration of Disposable Diaper

FIG. 1 is an exploded plan view of a disposable diaper 10 according to the present embodiment. It should be noted that the exploded plan view of FIG. 1 is a diagram in which leg gathers 75 and leg side gathers 80 are in an expanded state such that wrinkles are not formed in a topsheet 50 and side flap 70, for example, that configure the disposable diaper 10, but for the sake of description, the leg side gathers 80 are illustrated in a contracted state.

Figure 2:
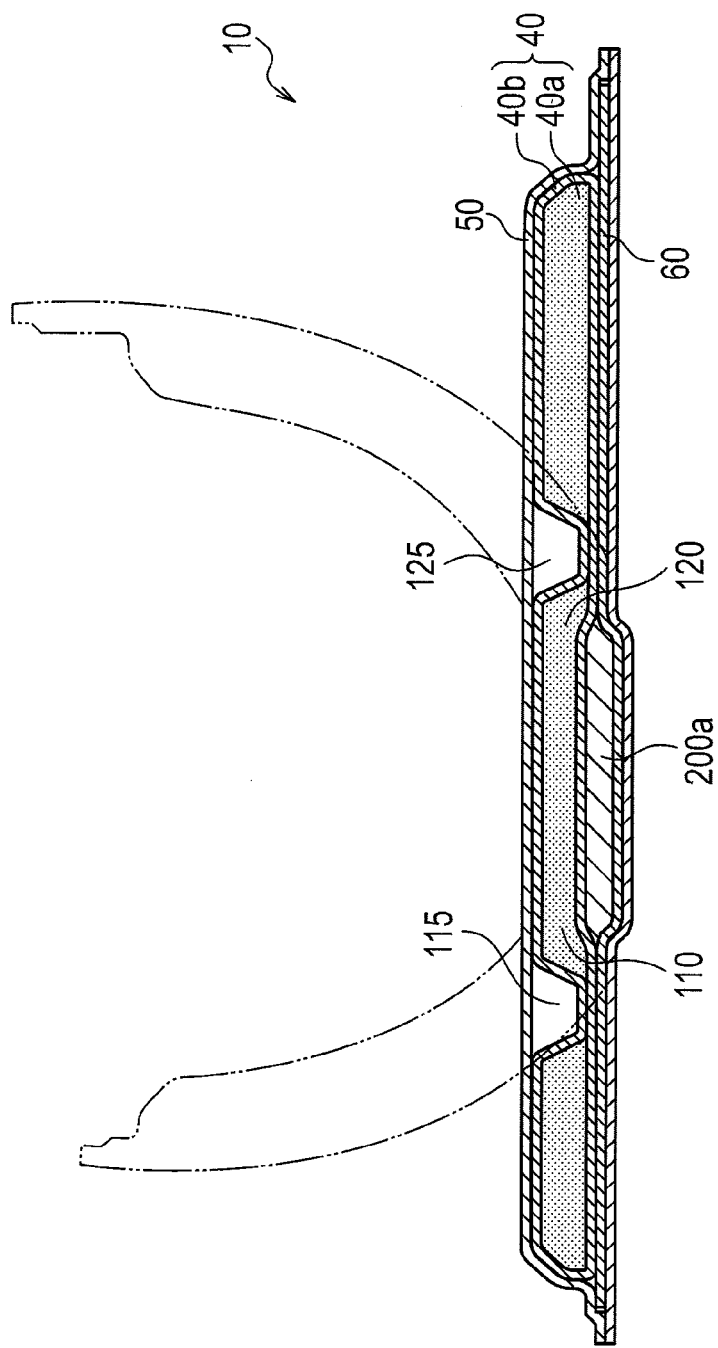
FIG. 2 is a cross-sectional view of the disposable diaper 10 along an F2-F2 line shown in FIG. 1.

FIG. 2 is a cross-sectional view of the disposable diaper 10 along an F2-F2 line shown in FIG. 1.

Figure 4:
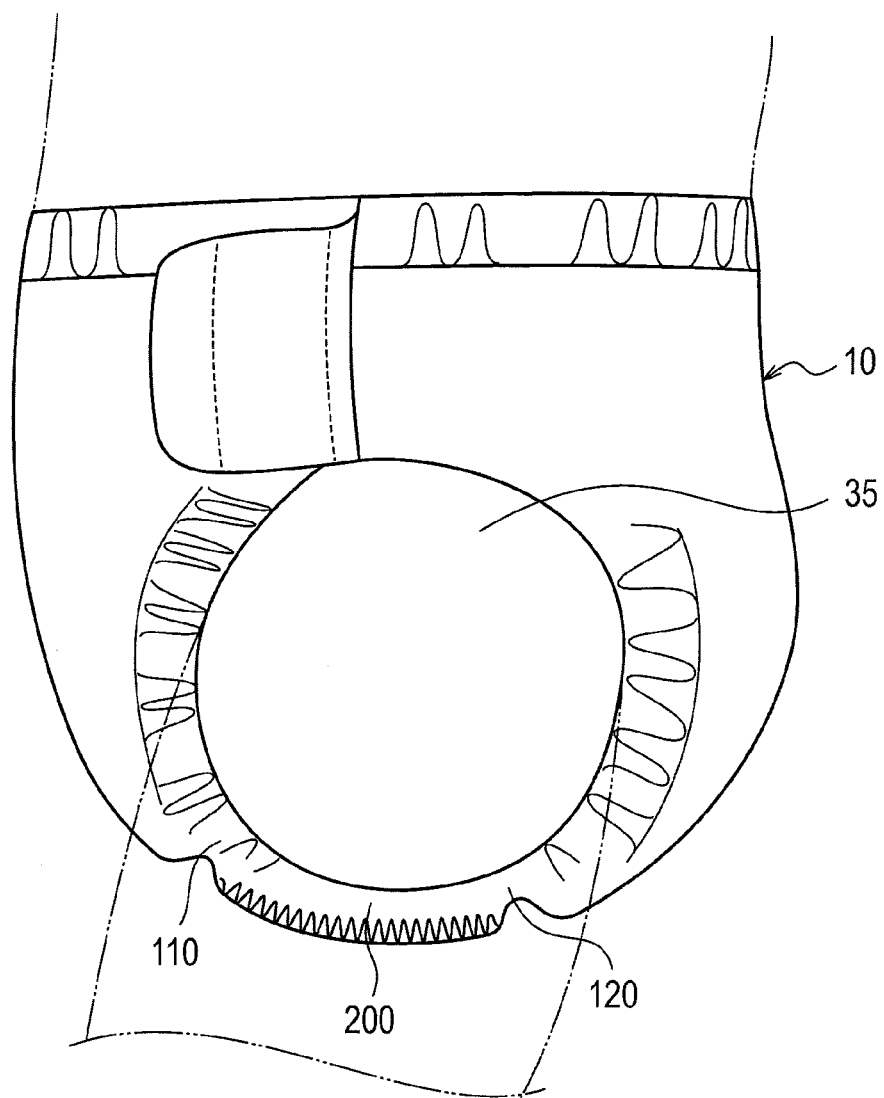
FIG. 4 is a diagram schematically illustrating the state when the disposable diaper 10 according to the embodiment of the present invention is worn by a wearer.
Figure 5B:
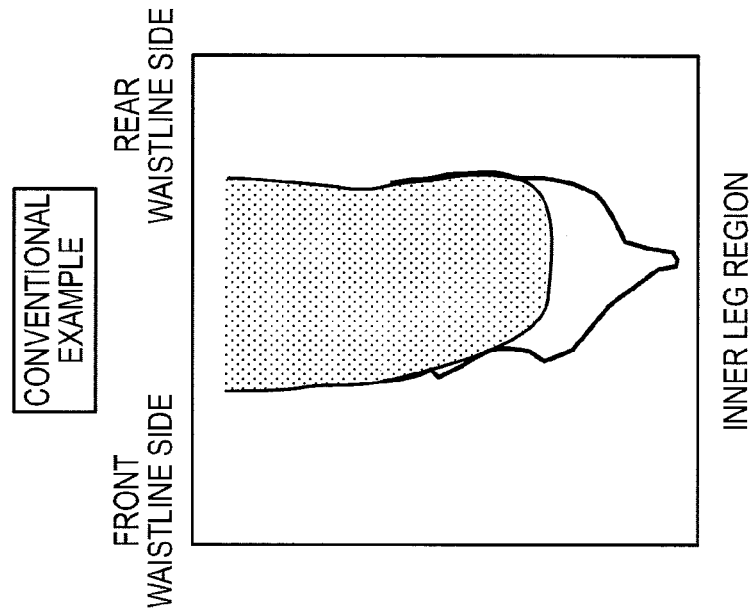
FIGS. 5a and 5b are diagrams schematically illustrating the result of a CT scan of the state when the disposable diaper 10 according to the embodiment of the present invention and a conventional disposable diaper are worn by a wearer.
Figure 5A:
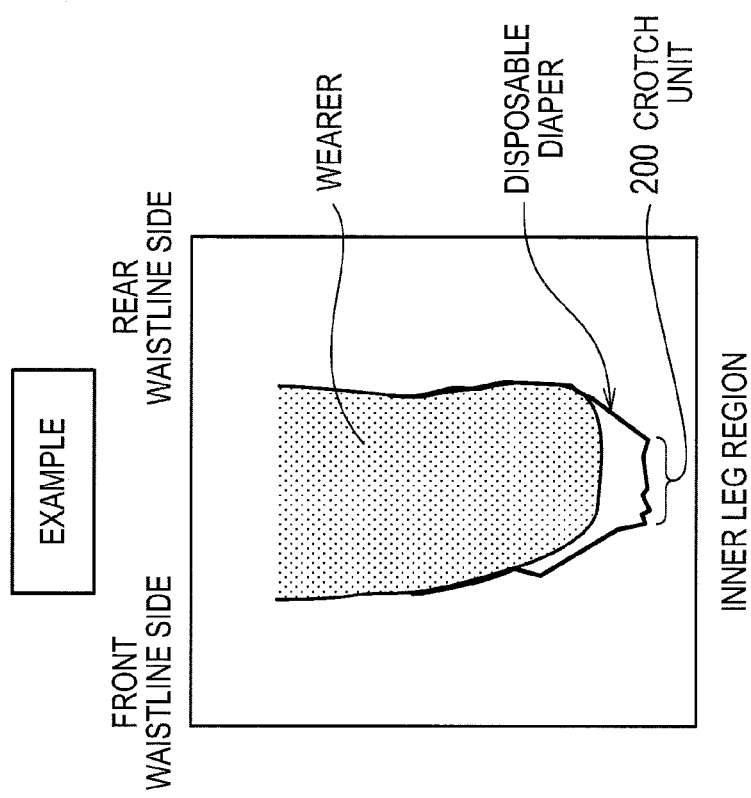

As illustrated in FIG. 1 or FIG. 2, the disposable diaper 10 includes a front waistline region 20, a crotch region 25, and a rear waistline region 30. The front waistline region 20 is a portion that is in contact with the front waistline unit of the wearer. Furthermore, the rear waistline region 30 is a portion that is in contact with the rear waistline unit of the wearer. The crotch region 25 is positioned between the front waistline region 20 and the rear waistline region 30. Furthermore, a pair of leg hole opening units 35 (see FIG. 4) is formed in the disposable diaper 10.

In the present embodiment, the direction from the front waistline region 20 to the rear waistline region 30 is called the product longitudinal direction L, and the direction perpendicular to the product longitudinal direction L is called the product widthwise direction W.

The disposable diaper 10 includes an absorber 40 running across the crotch region 25 and extending from the crotch region 25 towards at least one of the front waistline region 20 and the rear waistline region 30. The absorber 40 is configured by an absorbent core 40a and a core wrap 40b.

The absorbent core 40a is same as in the conventional disposable diaper, and can be configured appropriately by using popular components and materials, such as ground pulp and high absorbent polymer. The absorbent core 40a is wrapped by the sheet-like core wrap 40b. The core wrap 40b is a sheet for wrapping the absorbent core 40a. A part of at least the skin surface side of the core wrap 40b is configured by various nonwoven fabrics or a tissue sheet having permeability. For example, an air-through nonwoven fabric, a spunbond nonwoven fabric, or an SMS (spunbond-meltblown-spunbond) nonwoven fabric having a mass of approximately 10 to 30 g/m², or a tissue sheet having a mass of approximately 10 to 30 g/m² can be used.

On the top side (skin contact surface side) of the absorber 40 is provided the liquid-permeable topsheet 50. Furthermore, on the back side (non-skin contact surface side) of the absorber 40 is provided a liquid-impermeable backsheet 60.

A side flap 70 is provided in each side edge in the product widthwise direction W of the absorber 40. The side flaps 70 are made of one or two or more pieces of nonwoven fabrics overlapping one another. Furthermore, a fastening tape 90 is provided in each of the pair of side flaps 70.

The fastening tape 90 extends along the product widthwise direction W in the front waistline region 20 and the rear waistline region 30, and holds the disposable diaper 10 onto the body of the wearer. In the present embodiment, the waistline retaining unit is configured by the front waistline region 20, the rear waistline region 30, and the fastening tape 90.

The top side (topsheet 50 side) of the absorber 40 is formed along the leg hole opening units 35, and includes a pair of leg gathers 75 (leg elastic units) that can expand and contract in the product longitudinal direction L. The leg gathers 75 are formed by an elastic nonwoven sheet.

Specifically, at least in the crotch region 25, the nonwoven sheet is preferred to have a width of 5 mm (width in the product widthwise direction W in the natural state of the disposable diaper 10) or more and 35 mm or less. When the width is less than 5 mm, the effect of the sheet running, substantially on its surface, along the area around the legs of the wearer is not exhibited, and if the width exceeds 35 mm, the region along the area around the legs widens as a result of which the nonwoven sheet may easily shift in towards the body of the wearer or may turn over.

The ratio of expansion and contraction of the leg gathers 75 is preferably between 1.6 and 2.4 times. In the present embodiment, the ratio of expansion and contraction of the leg gathers 75 is set to 2.0 times.

The ratio of expansion and contraction of the leg gathers 75 implies the extent of stretching of the leg gathers 75 in the stretching direction thereof (product longitudinal direction L), and is stipulated as below:

The ratio of expansion and contraction of the leg gathers 75=(Length of the leg gathers 75 during maximum extension)/(Length of the leg gathers 75 in the natural state)

It should be noted that the ratio of expansion and contraction of the leg gathers 75 is measured as described below.

If the disposable diaper 10 is inserted in a package, take the diaper out of the package, and use a sample that has been kept in such a condition for 12 hours in an ambient temperature of 20° C.±2° C., and a relative humidity of 60%±5% RH.

Next, use a spring measure (tape: covered with glass fiber reinforced vinyl chloride) manufactured by Shinwa Rules Co., Ltd., keep it along the area to be measured, and measure the length of the disposable diaper 10 in this state, that is, the length of the leg gathers 75 when the disposable diaper 10 is in the natural state, and the length of the leg gathers 75 when the disposable diaper 10 is extended from its natural state until wrinkles caused by the elastic members are not visible to the naked eye. The above measurement was performed for 10 samples, and the average value was assumed as the aforementioned length.

Hereinafter, the measurement of the "length" described in the specification will be performed based on the aforementioned measuring method.

Furthermore, a gap between the inner ends of the pair of the left-right leg gathers 75 in the product widthwise direction W widens from the crotch region 25 towards the front waistline region 20, and also widens from the crotch region 25 towards the rear waistline region 30. Additionally, the gap (D1 in the figure) at the ends of the front waistline region 20 of the pair of left-right leg gathers 75 is narrower than the gap (D2 in the figure) at the ends of the rear waistline region 30 of the pair of left-right leg gathers 75. The gap is the distance between the inner ends of the pair of left-right leg gathers 75 in the product widthwise direction W that is measured after expanding and holding the disposable diaper 10 from the natural state to the state when no wrinkles are formed, in the product longitudinal direction L and the product widthwise direction W.

The extension of the skin surface of the body of the wearer is particularly large in the hip, and is remarkable at a position towards the outer widthwise direction. Furthermore, the leg gathers 75 are in contact with the body of the wearer. Because D2>D1, even when the movement of the wearer is added to the disposable diaper 10, the leg gathers 75 in the hip can extend while being in contact with the body, and even when the amount of change of the stretching is large, the leg gathers 75 do not become stiff. Therefore, the shifting of the disposable diaper 10 can be controlled by the leg gathers 75.

Furthermore, on the inner side (towards the center of the product widthwise direction W) of the pair of leg gathers 75 are provided a pair of leg side gathers 80 (side elastic units) that extend along the product longitudinal direction L. The leg side gathers 80 have a joining portion 81 that is joined with the absorber 40 (specifically, the topsheet positioned on the skin contact surface side of the absorber 40), and a free end portion 82 that is positioned on the opposite side of the joining portion 81 and in which elastic members (not shown in the figure) are arranged. As for the leg side gathers 80, when the diaper is worn, the joining portion 81 rises up as the proximal end and the free end portion 82 is in contact with the skin of the wearer as the apex. The disposable diaper 10 may also include waist gathers arranged along the product widthwise direction W in the front waistline region 20 and the rear waistline region 30.

A first inflected unit 110 and a second inflected unit 120 are formed in the absorber 40. The first inflected unit 110 and the second inflected unit 120 extend along the product widthwise direction W. The second inflected unit 120 is positioned towards the rear waistline region 30 from the first inflected unit 110. The first inflected unit 110 and the second inflected unit 120 form the curved base points of the disposable diaper 10.

In the present embodiment, a notch 115 (notch 125) is formed in the region outside the product longitudinal direction L of the first inflected unit 110 (second inflected unit 120). The notch 115 is formed in a region corresponding to the first inflected unit 110. Similarly, the notch 125 is formed in a region corresponding to the second inflected unit 120. The notch 115 and the notch 125 is a region in which the absorbent core 40a configuring the absorber 40 does not exist. In the present embodiment, the notch 115 and the notch 125 correspond to a low rigidity unit in which the basis weight of the absorbent core 40a is lower than that of the other portion of the absorbent core 40a.

It should be noted that instead of forming the notch 115 and the notch 125, the region of the notch 115 and the notch 125 may be such that the basis weight of the absorbent core 40a is lower than that of the other portion of the absorbent core 40a.

The basis weight of the absorbent core 40a is measured as described below. First of all, an electronic balance is used to measure the mass of the absorbent core 40a in the target region. Secondly, the measured mass is divided by the area of the side surfaces of the target region at the topsheet side, and the result in terms of mass per 1 m$^2$ is considered as the basis weight of the absorbent core 40a. The notch 115 and the notch 125 are formed in order to improve the condition of the first inflected unit 110 and the second inflected unit 120. In the present embodiment, the notch 115 and the notch 125 exist along the edges in the product longitudinal direction L of the crotch unit 200. It should be noted that even though the notch 115 and the notch 125 are formed, the absorbent core 40a positioned in the front waistline region 20 and the rear waistline region 30, and the absorbent core 40a positioned in the crotch region 25 are preferred to be in continuation rather than being completely separate.

As the notch 115 and the notch 125 run towards the outer side of the product widthwise direction W, the length in the product longitudinal direction L (natural state of the disposable diaper 10) keeps on widening. As a result of such a shape, the outer side of the product widthwise direction W of the absorbent core 40a can contract easily, and thus, as described later, a flat "bottom unit" is formed in the disposable diaper 10. Furthermore, the absorbent core 40a positioned towards the front waistline region 20 from the notch 115, and the absorbent core 40a positioned towards the rear waistline region 30 from the notch 125 rise up from the "bottom unit", and can easily curve along the roundness of the body of the wearer (the abdomen and the hip).

Furthermore, the edge towards the front waistline region 20 (rear waistline region 30) of the notch 115 (notch 125) is arc shaped. The shape of the edge of the notch 115 (notch 125) is such that the center of the arc is positioned in the rear waistline region 30 (front waistline region 20) from the edge. As a result of such a shape, the deformation along the roundness of the body of the wearer occurs more easily and remarkably.

The crotch unit 200 is formed in the crotch region 25, specifically, between the first inflected unit 110 and the second inflected unit 120. The crotch unit 200 is formed so as to more easily maintain the flat shape as compared to the other portions of the absorber 40. The crotch unit 200 includes the crotch stretch unit 200a that can be extended and contracted in at least the product longitudinal direction L or the product widthwise direction W. That is, the first inflected unit 110 and the second inflected unit 120 are formed by the rigidity difference between the area contracted by the contraction of the crotch stretch unit 200a and the area other than the contracted area.

Rather than intersecting the front waistline region 20, the rear waistline region 30, and the fastening tape 90 that configure the waistline retaining unit, the crotch unit 200 is provided independently from the front waistline region 20, the rear waistline region 30, and the fastening tape 90.

(2) Shape of Crotch Unit

Figure 3:
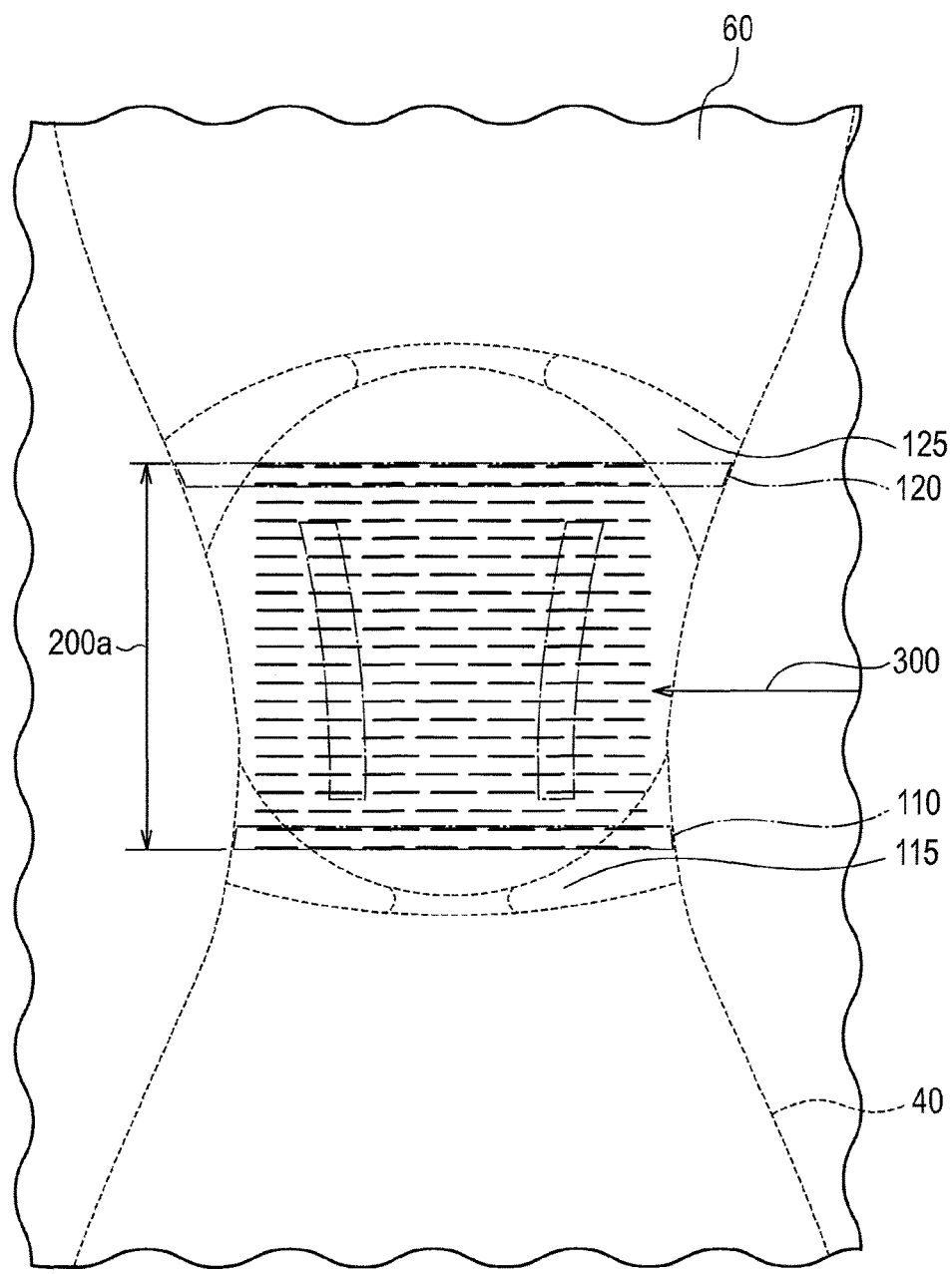
FIG. 3 is a magnified plan view of a crotch unit 200 according to the embodiment of the present invention, as seen from the backsheet 60 side.

Next, the shape of the crotch unit 200 will be described. FIG. 3 is a magnified plan view of the crotch unit 200 as seen from the backsheet 60 side.

As described above, the crotch unit 200 includes the crotch stretch unit 200a. In the present embodiment, an elastic sheet is used as the crotch stretch unit 200a. A stretch film formed by melting a thermoplastic elastomer resin, such as urethane and styrene, and then converting into the shape of a film, a nonwoven fabric formed from such elastic fibers, or a composite sheet formed by pasting together non-elastic sheets that have been partially cut into a stretch film and elastic nonwoven fabric, or have been made fragile can be used as the elastic sheet.

Furthermore, rather than an elastic sheet, the crotch stretch unit 200a can also be configured through an alternate, parallel arrangement of thread-like or band-like stretchable elastic members made from polyurethane elastic fibers and natural rubber. In such a case, in view of the rigidity of the absorbent core 40a and the rigidity of the other members configuring the disposable diaper 10, the thickness of the elastic members and the arrangement pitch can be selected appropriately, however, when the main body of the disposable diaper 10 is in the natural state (un-expanded state), the entire side edge region in the product widthwise direction W of the absorbent core 40a is preferable to be in a contracted state.

In the present embodiment, the crotch unit 200 can be extracted and contracted along the product longitudinal direction L. As a result, the front waistline region 20 and the rear waistline region 30 can rise up easily due to the contraction of the crotch unit 200, thus improving the fitting of the disposable diaper 10 on the wearer. Specifically, the stretch rate of the crotch stretchable potion 200a preferably is 1.2 times or more and 1.8 times or less. In the present embodiment, the stretch rate of the crotch stretch unit 200a is set to 1.4 times.

The ratio of expansion and contraction of the crotch stretch unit 200a implies the extent of the expansion and contraction of the crotch stretch unit 200a in the direction of expansion and contraction (product longitudinal direction L), and is stipulated as below:

> The ratio of expansion and contraction of crotch stretch unit 200a=(Length of the crotch unit during maximum extension)/(Length of the crotch unit in the natural state)

It should be noted that the ratio of expansion and contraction of the crotch stretch unit 200a is measured as described below.

If the disposable diaper 10 is inserted in a package, take the diaper out of the package, and use a sample that has been kept in such a condition for 12 hours in an ambient temperature of 20° C.±2° C., and a relative humidity of 60%±5% RH.

Next, use a spring measure (tape: covered with glass fiber reinforced vinyl chloride) manufactured by Shinwa Rules Co., Ltd., keep it along the area to be measured, and measure the length of the disposable diaper 10 in this state, that is, the length of the crotch unit 200a when the disposable diaper 10 is in the natural state, and the length of the crotch unit 200a when the disposable diaper 10 is extended from its natural state until wrinkles caused by the elastic members are not visible to the naked eye.

The above measurement was performed for 10 samples, and the average value was assumed as the aforementioned length.

As a result of such a ratio of expansion and contraction, it is possible to favorably follow the expansion and contraction of the skin of the wearer. This is because when the skin of the wearer extends and contracts, for example, when a slouchy posture is adopted where the front side of the body contracts in the hip of the wearer, the skin in the hip extends by approximately 30% as compared to the state when the body has been extended.

That is, when the ratio of expansion and contraction is 1.2 times or less, the contraction in the natural state of the disposable diaper 10 is insufficient, and as compared to non-contraction, the difference in the ease of curving of the disposable diaper 10 is small because of which the inflected unit is not formed at the desired position. On the other hand, when the ratio of expansion and contraction is more than 1.8 times, the contraction size in the contraction direction of the crotch stretch unit 200a becomes too large, the crotch stretch unit 200a easily comes in closer contact with the body of the wearer rather than running along it in the region where the crotch stretch unit 200a exists, as a result of which the disposable diaper 10 easily shifts to the lower side of the wearer. Furthermore, as described above, the ratio of expansion and contraction of the leg gathers 75 is preferably between 1.6 and 2.4 times, and the ratio of expansion and contraction of the leg gathers 75 is preferably higher than the ratio of expansion and contraction of the crotch stretch unit 200a. The ratio of expansion and contraction of the leg gathers 75 is also stipulated in the same way as the aforementioned crotch unit 200.

The crotch stretch unit 200a can be extended and contracted in the product longitudinal direction L, and is formed in the crotch unit 200.

A low stretch region 300 in which the ratio of expansion and contraction is lower than the crotch stretch unit 200a in the natural state of the disposable diaper 10 is formed between the leg gathers 75 and the crotch stretch unit 200a. The ratio of expansion and contraction of the low stretch region 300 is also stipulated in the same way as the aforementioned crotch unit 200. In the present embodiment, the low stretch region 300 has almost no stretchability.

The leg gathers 75 are longer than the crotch stretch unit 200a in the product longitudinal direction L, and are provided on the outer side from the crotch stretch unit 200a in the product widthwise direction W.

Furthermore, the end of the free end portion 82 of the leg side gathers 80 in the product longitudinal direction L is joined with the topsheet 50. The joining portion 81 is arranged between the crotch stretch unit 200a and the leg gathers 75, in the product widthwise direction W.

The size of the crotch unit 200 along the product longitudinal direction L is 30 mm or more and 150 mm or less in the natural state of the disposable diaper 10. When the wearer is made to lie down on his/her back on a level bed, and an observation is made from the side of the wearer, the size is preferable so that the abdominal side passes through the belly button of the wearer and does not come in contact with an imaginary line parallel to the bed top, and the back side fits into a crotch of the wearer without coming in contact with the bed.

When the size is less than 30 mm, the crotch unit 200 cannot sufficiently cover the crotch of the wearer, and it becomes difficult for the crotch unit 200 to come close to the body of the wearer. On the other hand, when the size exceeds 150 mm, it becomes difficult for the crotch unit 200 to fit within the crotch of the wearer. Because the disposable diaper 10 is held in place by the region around the waistline in the abdominal side and back side of the wearer, when the crotch unit 200 (crotch stretch unit 200a) extends in the region, the crotch stretch unit 200a comes in close contact with the body of the wearer due to the contractile force of the crotch stretch unit 200a. When the crotch stretch unit 200a comes in close contact with the body of the wearer, it becomes difficult for a bodily waste retaining space to form between the body and the disposable diaper 10. This is also not preferable because the disposable diaper 10 can easily shift towards the lower side due to the movement of the wearer.

Furthermore, the crotch unit 200 is formed at a position that includes the center of the disposable diaper 10 in the product longitudinal direction L. Furthermore, the length of the rear waistline region 30 in the product longitudinal direction L in the natural state of the disposable diaper 10 is longer than the length of the front waistline region 20 in the product longitudinal direction L in the natural state of the disposable diaper 10.

Specifically, the ratio of the length of the rear waistline unit in the product longitudinal direction with the length of the front waistline unit in the product longitudinal direction is 1.1 or more and 1.6 or less, and preferably 1.5 or less. If the ratio exceeds 1.6, the balance between the abdominal side and back side of the disposable diaper 10 is disturbed, and when the crotch unit 200 of the diaper runs along the crotch region 25, the front waistline region 20 comes in very close contact with the body, and the rear waistline region 30 is covered by more than the required amount. Specifically, because the hip of the body of the wearer is generally protruding out more than the lower abdomen, by matching the crotch unit in which the "bottom unit" is formed with the crotch of the wearer, and then setting the ratio within the aforementioned range, the disposable diaper 10 seems to have a more suitable shape for complex body shapes. That is, the partial stiffness of the disposable diaper 10 due to the occurrence of a portion with an insufficient size, and the unnecessary space between the disposable diaper 10 and the body of the wearer due to the occurrence of a portion with an excess size can be prevented.

Furthermore, particularly in the case of an infant or toddler who is in the stage prior to walking, or has just started walking, the body is preferably bent towards the abdominal side with a rounded posture. In such a posture, the skin of the hip stretches easily, and by setting the ratio within the aforementioned range, the disposable diaper will become suitable for the body of an infant or toddler that easily takes such a posture.

As an example, the front waistline region 20 is set to 130 mm, the crotch unit 200 is set to 80 mm, and the rear waistline region 30 is set to 190 mm with respect to the product length of 400 mm (product longitudinal direction L) of the disposable diaper 10. In such a case, the ratio of the length of the front waistline region 20 with the length of the rear waistline region 30 is approximately 1.46. By setting such a ratio, not only the crotch unit 200, but the entire product longitudinal direction L of the disposable diaper 10 can further be set along the body of the wearer.

In the present embodiment, the width of the crotch stretch unit 200a in the product widthwise direction W in the natural state of the disposable diaper 10 and the width of the absorbent core 40a in the crotch stretch unit 200a in the natural state of the disposable diaper 10 are almost the same in at least one part. "Almost the same" implies that the difference in the width of the absorbent core 40a and the crotch stretch unit 200a with respect to the width of the absorbent core 40a is within 20%.

Specifically, the width of the crotch stretch unit 200a in the product widthwise direction W in the natural state of the disposable diaper 10 is preferably between 50 and 110 mm, and more preferably 90 mm or less.

In the present embodiment, the width of the absorbent core 40a along the product widthwise direction W in the natural state of the disposable diaper 10 is the narrowest in the region where the crotch unit 200 is formed.

If the width of the crotch stretch unit 200a is too narrow as compared to the absorbent core 40a, the effect of maintaining the crotch stretch unit 200a in a flat shape is difficult to exhibit. On the other hand, if the width of the crotch stretch unit 200a is too wide, a region in which the absorbent core 40a is not arranged is contracted, and the rigidity around the crotch stretch unit 200a increases. Therefore, the crotch stretch unit 200a maybe caught easily in the femur of the wearer. Furthermore, because the diaper is worn in a state where the crotch stretch unit 200a is relatively contracted in a region where the absorbent core 40a does not exist, overlapping of members may occur easily and the crotch stretch unit 200a may harden as a result of which the wearing comfort may be missed out.

Furthermore, the distance between the absorbent core 40a in the crotch stretch unit 200a and the inner ends in the product widthwise direction W of the leg gathers 75, in the natural state of the disposable diaper 10, is preferably between 30 and 60 mm. As a result, the crotch stretch unit 200a can easily come close to the body of the wearer by the leg gathers 75, and furthermore, the crotch stretch unit 200a can come close to the body of the wearer while maintaining an appropriate gap.

Additionally, in the natural state of the disposable diaper 10, the width of the crotch unit 200, specifically, the crotch stretch unit 200a, along the product widthwise direction W, is narrower than the width of the absorbent core 40a along the product widthwise direction W in a region overlapping the crotch unit 200.

However, in the natural state of the disposable diaper 10, the difference between the width of the crotch unit 200 along the product widthwise direction W and the width of the absorbent core 40a along the product widthwise direction W in a region overlapping the crotch unit 200 is 20% or less.

Furthermore, in the natural state of the disposable diaper 10, the portion where the width of the crotch unit 200 is the narrowest is preferred to be arranged across a position that is 15 to 45 mm towards the front waistline region 20, and more preferably across a position that is 25 to 35 mm towards the front waistline region 20 from the central line of the disposable diaper 10 along the product widthwise direction W.

The position at which the left and the right femurs are closest to each other is towards the front waistline from the center in the front-and-rear direction of the body of the wearer. Therefore, by having an arrangement as described above, the inflected unit can be provided at a position matching more the shape of the body, and the crotch unit 200 can be made to run along the crotch of the wearer while improving the wearing comfort.

(3) Operation and Effect

According to the disposable diaper 10, because the front and back inflected units (first inflected unit 110 and second inflected unit 120) and the crotch stretch unit 200a form a "bottom unit", the crotch unit 200 of the disposable diaper 10 is arranged at a position close to the body of the wearer. Therefore, the crotch unit 200 can run along a position close to the body even when a weight or load is exerted from the outside.

Furthermore, because the leg gathers 75 exist along the leg hole opening units 35, the leg hole opening units 35 are positioned in the area around the legs of the wearer, and the occurrence of a space between the disposable diaper 10 and the body of the wearer in the area around the leg hole opening units 35 is prevented. Therefore, the leakage of the bodily waste and the shifting of the position of the disposable diaper 10 can be prevented.

Additionally, a low stretch region 300 exists between the leg gathers 75 and the crotch stretch unit 200a. Thus, particularly in an inner leg unit of the wearer, the crotch unit 200 is arranged at a position close to the body, the leg hole opening units 35 can rise up towards the body of the wearer with the crotch unit 200 as the reference position, and the diaper can be made to run continuously along the area around the legs of the wearer in a relatively favorable manner.

Furthermore, the crotch stretch unit 200a and the leg gathers 75 exist within the same region, and the crotch stretch unit 200a and leg gathers 75 contract in the product longitudinal direction L. Therefore, due to the crotch stretch unit 200a, the absorbent core 40a of the crotch region 25 (crotch unit) of the disposable diaper 10 contracts, the contraction of the leg gathers 75 is not easily affected by the absorbent core 40a, and thus the leg gathers 75 contract easily. Particularly, because the crotch stretch unit 200a is provided in the crotch unit, the leg gathers 75 of the crotch unit can contract in a relatively easy manner.

As a result, the leg gathers 75 easily come in contact with the area around the legs of the wearer, and particularly, the close contact of the leg gathers 75 in the inner leg unit where a space can occur easily due to the weight of the absorber 40 can further be improved. Furthermore, by providing the crotch stretch unit 200a, the rate of expansion and contraction of the leg gathers 75 can be reduced, alternatively, the stress due to the leg gathers 75 can be reduced, and the leg gathers 75 can be brought in close contact with the area around the legs in a relatively easier manner.

Moreover, in the natural state of the disposable diaper 10, the leg gathers 75 (leg elastic unit) are longer than the crotch unit 200 in the product longitudinal direction L.

Furthermore, the low stretch region 300 having a lower rate of expansion and contraction as compared to the crotch unit 200 in the natural state of the disposable diaper 10 is formed between the leg gathers 75 and the crotch unit 200.

Therefore, while the periphery including the leg gathers 75 and the crotch unit 200 are contracted, the low stretch region 300 is more difficult to contract as compared to the periphery including the leg gathers 75 and the crotch unit 200, because of which at the time of wearing the disposable diaper 10, the low stretch region 300 bulges easily, and the crotch region 25 of the disposable diaper 10 can be easily formed into what is called puffed sleeve shape. When the crotch region 25 of the disposable diaper 10 takes the shape of a puffed sleeve, it is easy to secure air permeability in the groin of the wearer. Also, because there is no interference with the movement of legs, the wearer does not experience any uncomfortable feeling.

In the present embodiment, in the natural state of the disposable diaper 10, the gap in the product widthwise direction W of the leg gathers 75 widens from the crotch region 25 towards the front waistline region 20, and widens from the crotch region 25 towards the rear waistline region 30.

Therefore, when the disposable diaper 10 is worn, the clearance in the front and rear ends of the leg gathers 75 can be reduced, or the leg gathers can be arranged by crossing each other. Thus, the leg gathers 75 can be made to run continuously, without any gap, along the area around the legs of the wearer in a favorable manner.

In the present embodiment, in the natural state of the disposable diaper 10, the width of the leg gathers 75 in the product widthwise direction W is 5 mm or more, in the natural state of the disposable diaper 10.

Therefore, the leg gathers 75 can run, on its surface, along the area around the legs of the wearer because of which the occurrence of a space between the disposable diaper 10 and the body of the wearer in the periphery of the leg hole opening units 35 is prevented more certainly.

(4) Other Embodiments

So far, the present invention is disclosed through the above embodiment. However, it should not be interpreted that the statements and drawings constituting a part of the present disclosure limit the present invention. From this disclosure, a variety of alternate embodiments, examples, and applicable techniques will become apparent to one skilled in the art.

For example, in the aforementioned disposable diaper 10, in order to make the stretching of the crotch unit 200 easy to recognize visually, a portion or a motif colored in a color different from the surroundings may be displayed in the topsheet 50 or the backsheet 60 of the crotch unit 200. For example, in FIG. 3, the region indicated by a dashed line may be colored in a color different from the surroundings.

Furthermore, in the disposable diaper according to the modification, rather than leg gathers formed from an elastic nonwoven sheet, leg gathers formed from thread-like elastic members may be provided.

In the aforementioned embodiment, an open-type disposable diaper was described as an example, however, the present invention is also applicable to a pant-type disposable diaper. As regards a pant-type diaper having a waistline opening unit and a pair of leg hole opening units formed by joining both left-right edges of an outer-layer sheet forming the front waistline region and the rear waistline region, the outer-layer sheet of the front waistline region and the rear waistline region includes elastic elements that can be expanded and contracted in the product widthwise direction W, and by contracting the elastic elements, the disposable diaper is held in the waistline of the wearer. That is, the area in which both left-right edges extending in the product longitudinal direction L are joined becomes the waistline retaining unit.

As described above, it is of course that the present invention includes various embodiments and the like not described here. Therefore, the technical range of the present invention is to be defined only by the inventive specific matter according to the adequate claims from the above description.

The invention claimed is:
1. A disposable diaper, comprising:
a front waistline region;
a rear waistline region;
a crotch region positioned between the front waistline region and the rear waistline region;
a pair of leg hole opening units;
an absorber running across the crotch region and extending in the front waistline region and the rear waistline region;
a product longitudinal direction from the front waistline region towards the rear waistline region;
a product widthwise direction that is perpendicular to the product longitudinal direction;
a waistline retaining unit extending along the product widthwise direction in the front waistline region and the rear waistline region, and configured to hold the disposable diaper onto a body of a wearer;
a crotch stretch unit that is formed in the crotch region, is completely apart from the waistline retaining unit in the product longitudinal direction, and is configured to expand and contract in at least the product longitudinal direction; and
a pair of leg elastic units respectively formed along the pair of leg hole opening units, the pair of leg elastic units extending in the front and rear waistline regions and being configured to expand and contract in at least the product longitudinal direction;
wherein
the crotch stretch unit is positioned on a non-skin contact surface side of the absorber and overlaps the absorber in a product thickness direction of the disposable diaper,
the leg elastic units are longer than the crotch stretch unit in the product longitudinal direction,
the crotch stretch unit has a front end and a rear end opposite to the front end in the product longitudinal direction, the pair of leg elastic units continuously extends, in the product longitudinal direction, beyond the front and rear ends of the crotch stretch unit, each of the leg elastic units is provided at an outer side from the crotch stretch unit in the product widthwise direction, a low stretch region having a lower ratio of expansion and contraction than the crotch stretch unit is formed between each of the leg elastic units and the crotch stretch unit, the crotch stretch unit is formed of an elastic sheet, and in a natural state of the disposable diaper, a width of the elastic sheet of the crotch stretch unit in the product widthwise direction is 50 to 110 mm.

2. The disposable diaper according to claim 1, wherein a gap between the leg elastic units in the product widthwise direction becomes wider from the crotch region towards the front waistline region and from the crotch region towards the rear waistline region.

3. The disposable diaper according to claim 2, wherein the gap includes a first gap in the front waistline region between the leg elastic units in the product widthwise direction, and a second gap in the rear waistline region between the leg elastic units in the product widthwise direction, and the first gap is narrower than the second gap.

4. The disposable diaper according to claim 1, wherein each of the leg elastic units is an elastic sheet, and a width of each of the leg elastic units along the product widthwise direction is 5 mm or more in the natural state of the disposable diaper where the leg elastic units are contracted.

5. The disposable diaper according to claim 1, further comprising:

a pair of side elastic units extending along the product longitudinal direction; and a topsheet provided on a skin contact surface side of the absorber, said skin contact surface side of the absorber being opposite to the non-skin contact surface side in the product thickness direction;

wherein each of the pair of side elastic units comprises:
a joining portion joined to the absorber; and
a free end portion opposite to the joining portion in the product widthwise direction, each of the pair of side elastic units includes an elastic member, ends of the free end portion in the product longitudinal direction are joined to the topsheet, and the joining portion is arranged between the crotch stretch unit and a corresponding one of the leg elastic units in the product widthwise direction.

6. The disposable diaper according to claim 1, wherein a ratio of expansion and contraction of each of the leg elastic units is higher than a ratio of expansion and contraction of the crotch stretch unit.

7. The disposable diaper according to claim 6, wherein the ratio of expansion and contraction of each of the leg elastic units is between 1.6 and 2.4 times.

8. The disposable diaper according to claim 6, wherein the ratio of expansion and contraction of the crotch stretch unit is between 1.2 and 1.8 times.

9. The disposable diaper according to claim 1, wherein an entirety of each of the leg elastic units is provided at the outer side from an entirety of the crotch stretch unit in the product widthwise direction.

10. The disposable diaper according to claim 1, wherein a width of the absorber along the product widthwise direction in the natural state of the disposable diaper is the narrowest in a region where the crotch stretch unit is arranged, and the natural state of the disposable diaper is a state where the leg elastic units are contracted.

11. The disposable diaper according to claim 1, wherein a width of the crotch stretch unit in the product widthwise direction is smaller than a width of the absorber along the product widthwise direction in a region where the crotch stretch unit overlaps the absorber in the product thickness direction of the disposable diaper.

12. The disposable diaper according to claim 1, wherein the crotch region includes a first notch at a first side of the crotch stretch unit, and
a second notch opposing the first notch in the product longitudinal direction and at a second side of the crotch stretch unit, and the first and second notches are formed in a region outside a longitudinal line along the product longitudinal direction and bisecting the absorber in the product widthwise direction.

13. The disposable diaper according to claim 1, wherein a ratio of expansion and contraction of the crotch stretch unit is higher in the product longitudinal direction than in the product widthwise direction.

14. The disposable diaper according to claim 1, wherein the absorber includes an absorbent core, and a width of the crotch stretch unit in the product widthwise direction is smaller than a width of the absorbent core in the product widthwise direction.

15. A disposable diaper, comprising:
a front waistline region;
a rear waistline region;
a crotch region positioned between the front waistline region and the rear waistline region;
a pair of leg hole opening units;
an absorber running across the crotch region and extending in the front waistline region and rear waistline region;
a product longitudinal direction from the front waistline region towards the rear waistline region;
a product widthwise direction perpendicular to the product longitudinal direction;
a waistline retaining unit extending along the product widthwise direction in the front waistline region and the rear waistline region, and configured to hold the disposable diaper onto a body of a wearer;
a crotch stretch unit formed in the crotch region and being completely apart from the waistline retaining unit in the product longitudinal direction, and the crotch stretch unit being configured to expand and contract in at least the product longitudinal direction; and
a pair of leg elastic units respectively formed along the pair of leg hole opening units, the pair of leg elastic units extending in the front and rear waistline regions and being configured to be expanded and contracted in at least the product longitudinal direction;

wherein the crotch stretch unit is positioned on a non-skin contact surface side of the absorber and overlaps the absorber in a product thickness direction of the disposable diaper, a low stretch region having a lower ratio of expansion and contraction than the crotch stretch unit is formed between each of the leg elastic units and the crotch stretch unit, the crotch stretch unit has a front end and a rear end opposite to the front end in the product longitudinal direction, the pair of leg elastic units continuously extends, in the product longitudinal direction, beyond the front and rear ends of the crotch stretch unit, each of the leg elastic units is provided at an outer side from the crotch stretch unit in the product widthwise direction, when the disposable diaper is worn, the low stretch region is configured to form a predetermined gap between the disposable diaper and the body of the wearer, by bulging more than the crotch stretch unit, the crotch stretch unit is formed of an elastic sheet, and in a natural state of the disposable diaper, a width of the elastic sheet of the crotch stretch unit in the product widthwise direction is 50 to 110 mm.

16. The disposable diaper according to claim 15, wherein an entirety of each of the leg elastic units is provided at the outer side from an entirety of the crotch stretch unit in the product widthwise direction.

17. The disposable diaper according to claim 15, wherein a gap between the leg elastic units in the product widthwise direction becomes wider from the crotch region towards the front waistline region and from the crotch region towards the rear waistline region.

18. The disposable diaper according to claim 17, wherein the gap includes a first gap in the front waistline region between the leg elastic units in the product widthwise direction, and a second gap in the rear waistline region between the leg elastic units in the product widthwise direction, and the first gap is narrower than the second gap.

19. The disposable diaper according to claim 15, wherein a width of the absorber along the product widthwise direction in the natural state of the disposable diaper is the narrowest in a region where the crotch stretch unit is arranged, and the natural state of the disposable diaper is a state where the leg elastic units are contracted.

20. The disposable diaper according to claim 15, wherein a width of the crotch stretch unit in the product widthwise direction is smaller than a width of the absorber along the product widthwise direction in a region where the crotch stretch unit overlaps the absorber in the product thickness direction of the disposable diaper.

21. The disposable diaper according to claim 8, wherein the crotch region includes a first notch at a first side of the crotch stretch unit, and a second notch opposing the first notch in the product longitudinal direction and at a second side of the crotch stretch unit, and the first and second notches are formed in a region outside a longitudinal line along the product longitudinal direction and bisecting the absorber in the product widthwise direction.

22. A disposable diaper, comprising:

a front waistline region;

a rear waistline region;

a crotch region positioned between the front waistline region and the rear waistline region;

a pair of leg hole opening units;

an absorber running across the crotch region and extending in the front waistline region and the rear waistline region;

a product longitudinal direction from the front waistline region towards the rear waistline region;

a product widthwise direction that is perpendicular to the product longitudinal direction;

a waistline retaining unit extending along the product widthwise direction in the front waistline region and the rear waistline region, and configured to hold the disposable diaper onto a body of a wearer;

a crotch stretch unit that is formed in the crotch region, is completely apart from the waistline retaining unit in the product longitudinal direction, and is configured to expand and contract in at least the product longitudinal direction; and a pair of leg elastic units respectively formed along the pair of leg hole opening units, the pair of leg elastic units extending in the front and rear waistline regions and being configured to expand and contract in at least the product longitudinal direction;

wherein the crotch stretch unit is positioned on a non-skin contact surface side of the absorber and overlaps the absorber in a product thickness direction of the disposable diaper, the leg elastic units are longer than the crotch stretch unit in the product longitudinal direction, the crotch stretch unit has a front end and a rear end opposite to the front end in the product longitudinal direction, the pair of leg elastic units continuously extends, in the product longitudinal direction, beyond the front and rear ends of the crotch stretch unit, each of the leg elastic units is provided at an outer side from the crotch stretch unit in the product widthwise direction, a low stretch region having a lower ratio of expansion and contraction than the crotch stretch unit is formed between each of the leg elastic units and the crotch stretch unit, the crotch stretch unit is formed of an elastic sheet, the absorber includes an absorbent core, and in a natural state of the disposable diaper, a difference between a width of the absorbent core and a width of the elastic sheet of the crotch stretch unit in the product widthwise direction with respect to the width of the absorbent core is within 20%.

23. A disposable diaper, comprising:

a front waistline region;

a rear waistline region;

a crotch region positioned between the front waistline region and the rear waistline region;

a pair of leg hole opening units;

an absorber running across the crotch region and extending in the front waistline region and the rear waistline region;

a product longitudinal direction from the front waistline region towards the rear waistline region;

a product widthwise direction that is perpendicular to the product longitudinal direction;

a waistline retaining unit extending along the product widthwise direction in the front waistline region and the rear waistline region, and configured to hold the disposable diaper onto a body of a wearer;

a crotch stretch unit that is formed in the crotch region, is completely apart from the waistline retaining unit in the product longitudinal direction, and is configured to expand and contract in at least the product longitudinal direction; and a pair of leg elastic units respectively formed along the pair of leg hole opening units, the pair of leg elastic units extending in the front and rear waistline regions and being configured to expand and contract in at least the product longitudinal direction;

wherein the crotch stretch unit is positioned on a non-skin contact surface side of the absorber and overlaps the absorber in a product thickness direction of the disposable diaper, the leg elastic units are longer than the crotch stretch unit in the product longitudinal direction, the crotch stretch unit has a front end and a rear end opposite to the front end in the product longitudinal direction, the pair of leg elastic units continuously extends, in the product longitudinal direction, beyond the front and rear ends of the crotch stretch unit, each of the leg elastic units is provided at an outer side from the crotch stretch unit in the product widthwise direction, a low stretch region having a lower ratio of expansion and contraction than the crotch stretch unit is formed between each of the leg elastic units and the crotch stretch unit, the crotch stretch unit is formed of an elastic sheet, the absorber includes an absorbent core, and in a natural state of the disposable diaper, a width of the elastic sheet of the crotch stretch unit in the product widthwise direction is at least 50% of a width of the absorbent core in the product widthwise direction.

24. A disposable diaper, comprising:

a front waistline region;

a rear waistline region;

a crotch region positioned between the front waistline region and the rear waistline region;

a pair of leg hole opening units;

an absorber running across the crotch region and extending in the front waistline region and the rear waistline region;

a product longitudinal direction from the front waistline region towards the rear waistline region;

a product widthwise direction that is perpendicular to the product longitudinal direction;

a waistline retaining unit extending along the product widthwise direction in the front waistline region and the rear waistline region, and configured to hold the disposable diaper onto a body of a wearer;

a crotch stretch unit that is formed in the crotch region, is completely apart from the waistline retaining unit in the product longitudinal direction, and is configured to expand and contract in at least the product longitudinal direction; and a pair of leg elastic units respectively formed along the pair of leg hole opening units, the pair of leg elastic units extending in the front and rear waistline regions and being configured to expand and contract in at least the product longitudinal direction;

wherein the crotch stretch unit is positioned on a non-skin contact surface side of the absorber and overlaps the absorber in a product thickness direction of the disposable diaper, the leg elastic units are longer than the crotch stretch unit in the product longitudinal direction, the crotch stretch unit has a front end and a rear end opposite to the front end in the product longitudinal direction, the pair of leg elastic units continuously extends, in the product longitudinal direction, beyond the front and rear ends of the crotch stretch unit, each of the leg elastic units is provided at an outer side from the crotch stretch unit in the product widthwise direction, a low stretch region having a lower ratio of expansion and contraction than the crotch stretch unit is formed between each of the leg elastic units and the crotch stretch unit, the crotch region includes a first notch extending in the product widthwise direction, and a second notch extending in the product widthwise direction, and the crotch stretch unit is between the first and second notches in the product longitudinal direction.

* * * * *